US012649941B2

(12) United States Patent
Yoshida et al.

(10) Patent No.: US 12,649,941 B2
(45) Date of Patent: Jun. 9, 2026

(54) PRACTICAL ENZYMATIC SYNTHESIS OF 3',3'-cGAMP

(71) Applicant: Yamasa Corporation, Choshi (JP)

(72) Inventors: Ko Yoshida, Choshi (JP); Kazuya Ishige, Choshi (JP)

(73) Assignee: Yamasa Corporation, Choshi (JP)

( * ) Notice: Subject to any disclaimer, the term of this patent is extended or adjusted under 35 U.S.C. 154(b) by 561 days.

(21) Appl. No.: 17/435,154

(22) PCT Filed: Feb. 28, 2020

(86) PCT No.: PCT/JP2020/008525
§ 371 (c)(1),
(2) Date: Aug. 31, 2021

(87) PCT Pub. No.: WO2020/179714
PCT Pub. Date: Sep. 10, 2020

(65) Prior Publication Data
US 2022/0136023 A1 May 5, 2022

(30) Foreign Application Priority Data

Mar. 1, 2019 (JP) ................................. 2019-037148

(51) Int. Cl.
| | |
|---|---|
| *C12P 19/36* | (2006.01) |
| *C12N 5/10* | (2006.01) |
| *C12N 9/12* | (2006.01) |
| *C12N 15/52* | (2006.01) |
| *C12N 15/70* | (2006.01) |

(52) U.S. Cl.
CPC ................ *C12P 19/36* (2013.01); *C12N 5/10* (2013.01); *C12N 9/1241* (2013.01); *C12N 15/52* (2013.01); *C12N 15/70* (2013.01); *C12Y 207/07* (2013.01); *C12N 2800/101* (2013.01)

(58) Field of Classification Search
CPC ......... C12P 19/36; C12N 5/10; C12N 9/1241; C12N 15/52; C12N 15/70; C12N 2800/101; C12Y 207/07
See application file for complete search history.

(56) References Cited

U.S. PATENT DOCUMENTS

| | | |
|---|---|---|
| 2014/0329889 A1 | 11/2014 | Vance et al. |
| 2015/0044724 A1 | 2/2015 | Tanabe et al. |
| 2017/0319680 A1 | 11/2017 | Ishii et al. |

FOREIGN PATENT DOCUMENTS

| | | |
|---|---|---|
| WO | WO-2013/086331 A1 | 6/2013 |
| WO | WO-2013/129427 A1 | 9/2013 |
| WO | WO-2014/179760 A1 | 11/2014 |
| WO | WO-2016/079899 A1 | 5/2016 |
| WO | WO-2020/051197 A1 | 3/2020 |

OTHER PUBLICATIONS

Kato et al., "Structural Basis for the Catalytic Mechanism of DncV, Bacterial Homolog of Cyclic GMP-AMP Synthase," Structure 23, 843-850. (Year: 2015).*
"NCBI Blast: Protein Sequence" downloaded Jan. 23, 2024 from <https://blast.ncbi.nlm.nih.gov/Blast.cgi#alnHdr_5GO3_A>. (Year: 2000).*
Zhu et al., "Structural Biochemistry of a Vibrio cholerae Dinucleotide Cyclase Reveals Cyclase Activity Regulation by Folates," Molecular Cell 55, 931-937. (Year: 2014).*
Siloto and Weslake, "Site saturation mutagenesis: Methods and applications in protein engineering." Biocatalysis and Agricultural Biotechnology 1: 181-189. (Year: 2012).*
Davies et al., "Coordinated regulation of accessory genetic elements produces cyclic di-nucleotides for *V. cholerae* virulence," Cell 149(2):358-370 (2012).
Gao et al., "Cyclic [G(2',5')pA(3',5')p] is the metazoan second messenger produced by DNA-activated cyclic GMP-AMP synthase," Cell 153(5):1094-1107 (2013).
Hallberg et al., "Hybrid promiscuous (Hypr) GGDEF enzymes produce cyclic AMP-GMP (3', 3'-cGAMP)," Proc. Natl. Acad. Sci. U.S.A. 113(7):1790-1795 (2016).
International Search Report for PCT International Patent Application No. PCT/JP2020/008525, Yoshida et al., "Practical Enzymatic Synthesis of 3',3'-cGAMP", filed Feb. 28, 2020, mailed Mar. 24, 2020 (7 pages).
Kranzusch et al., "Structure-guided reprogramming of human cGAS dinucleotide linkage specificity," available in PMC Aug. 28, 2015, published in final edited form as: Cell 158(5):1011-1021 (2014) (21 pages).
Extended European Search Report dated Jun. 9, 2022, for European Patent Application No. 20765610.9, Yoshida et al., "Practical Enzymatic Synthesis of 3',3'-cGAMP," filed Feb. 28, 2020 (10 pages).

(Continued)

*Primary Examiner* — Suzanne M Noakes
*Assistant Examiner* — Ciara A McKnight
(74) *Attorney, Agent, or Firm* — Clark & Elbing LLP

(57) ABSTRACT

In an enzymatic synthesis of 3',3'-cGAMP, other types of cyclic dinucleotides, c-di-GMP and c-di-AMP, are produced as by-products. One problem to be solved in order to establish a practical method for enzymatic synthesis of 3',3'-cGAMP is suppression of production of these other types of cyclic dinucleotides during the synthesis. As a result of intensive studies, the inventors of the present invention found a variation of 3',3'-cGAMP synthase by which the production of c-di-GMP and c-di-AMP is suppressed, and established a 3',3'-cGAMP enzymatic synthesis system using this variation of the enzyme to complete the present invention. This enzyme brings about significantly reduced production of c-di-GMP and c-di-AMP, compared to the wild-type 3',3'-cGAMP synthase. Accordingly, a production method using this enzyme makes it possible to reduce the production of other types of cyclic dinucleotides in comparison to conventional enzymatic synthesis methods, and efficiently synthesize 3',3'-cGAMP.

14 Claims, No Drawings
Specification includes a Sequence Listing.

(56)           References Cited

OTHER PUBLICATIONS

Kato et al., "Structural Basis for the Catalytic Mechanism of DncV, Bacterial Homolog of Cyclic GMP-AMP Synthase," Structure 23(5):843-850 (2015).

Opoku-Temeng et al., "Cyclic dinucleotide (c-di-GMP, c-di-AMP, and cGAMP) signalings have come of age to be inhibited by small molecules," Chem. Commun. (Camb). 52(60):9327-9342 (2016).

* cited by examiner

PRACTICAL ENZYMATIC SYNTHESIS OF 3',3'-cGAMP

SEQUENCE LISTING

The instant application contains a Sequence Listing which has been submitted electronically in ASCII format and is hereby incorporated by reference in its entirety. Said ASCII copy, created on Aug. 31, 2021, is named 51007-024001_Sequence_Listing_08_31_21_ST25 and is 13,752 bytes in size.

TECHNICAL FIELD

The present invention relates to mutants of 3',3'-cGAMP synthase suitable for synthesis of 3',3'-cGAMP and a practical method for synthesizing 3',3'-cGAMP using the mutants of the synthase.

BACKGROUND ART

3',3'-cGAMP is a signaling molecule involved in expression of bacterial pathogenic factors, and its bioactivity and signaling mechanisms have attracted much attention in recent years. For example, 3',3'-cGAMP has been recently shown to have immunostimulatory effects, and is expected to be applied as an adjuvant, antiviral agent, and anticancer agent (Patent Document 1).

Although chemical and enzymatic synthesis methods have been reported for the synthesis of 3',3'-cGAMP, no practical synthesis method has been developed, and only extremely limited amounts are available as research reagents (Non-Patent Documents 1, 2, and 3).

DncV derived from *Vibrio cholerae* (Vc DncV), which is a representative 3',3'-cGAMP synthase, not only synthesizes 3',3'-cGAMP from one ATP molecule and one GTP molecule, but also synthesizes cyclic-di-GMP (c-di-GMP) from two GTP molecules and cyclic-di-AMP (c-di-AMP) from two ATP molecules.

PRIOR ARTS

Patent Document

Patent Document 1: WO2016/079899

Non-Patent Documents

Non-Patent Document 1: Ming C. Hammond, et al, PNAS, 2016, 113(7), 1790-1795
Non-Patent Document 2: John J. Mekalanos, et al, Cell, 2012, 149, 358-370
Non-Patent Document 3: Dinshaw J. Patel, et al, Cell, 2013, 153(5), 1094-1107

SUMMARY OF INVENTION

Technical Problem

Due to properties of 3',3'-cGAMP synthase described above, c-di-GMP and c-di-AMP, which are similar cyclic dinucleotides, are produced as by-products in the enzymatic synthesis of 3',3'-cGAMP. In general, it is difficult to separate compounds with similar physicochemical properties from each other and to obtain high-purity products required for pharmaceuticals if a large amount of other cyclic dinucleotides is produced as by-products in the enzymatic synthesis of 3',3'-cGAMP.

Therefore, it is a challenge to establish a practical method for enzymatically synthesizing 3',3'-cGAMP in which by-products are suppressed in a synthetic step of these similar cyclic dinucleotides.

Solution to Problem

As a result of intensive investigation, the inventors of the present application found mutant-type 3',3'-cGAMP synthases that can suppress by-production of c-di-GMP and c-di-AMP and established an enzymatic synthesis system of 3',3'-cGAMP using the mutant-type synthases, and the invention was completed.

According to the present invention, there are provided [1] to [7] below.

[1] A mutant-type 3',3'-cGAMP synthase including one or more amino acid mutations selected from the group consisting of the following amino acid residues: Y117, N121, M130, K177, A292, and K350 of wild-type 3',3'-cGAMP synthase.

[2] The mutant-type 3',3'-cGAMP synthase according to [1], in which the one or more mutations contain at least one mutation selected from the group consisting of the following amino acid residues:
    Y117 (H, R, or K),
    N121 (I, G, A, V, L, or P),
    M130 (V, I, G, A, L, P, F, H, Y, or W),
    K177 (M, H, C, F, Y, or W),
    A292 (T, K, Y, S, F, W, R, or H), and
    K350 (E, D, M, N, Q, or C).

[3] The mutant-type 3',3'-cGAMP synthase according to [1], in which the one or more mutations contain at least one mutation selected from the group consisting of the following amino acid residues:
    Y117(H),
    N121(I),
    M130 (V, or F),
    K177 (M, H, or C),
    A292 (T, K, or Y), and
    K350 (E, D, or M).

[4] A polynucleotide encoding the mutant-type 3',3'-cGAMP synthase according to any one of [1] to [3].

[5] An expression vector including the polynucleotide according to [4].

[6] A transformant including the polynucleotide according to [4] or the expression vector according to [5].

[7] A method for producing 3',3'-cGAMP from one ATP molecule and one GTP molecule using an enzyme, in which the enzyme is the mutant-type 3',3'-cGAMP synthase produced by culturing the transformant according to [6].

Advantageous Effect of the Invention

The synthase of the present invention significantly suppresses by-production of c-di-GMP and c-di-AMP compared to wild-type 3',3'-cGAMP synthase. Therefore, the production method using the synthase can reduce the by-products of similar cyclic dinucleotides and synthesize 3',3'-cGAMP more efficiently than conventional enzymatic synthesis methods. Thus, the synthase of the present invention and the method for synthesizing 3',3'-cGAMP using the synthase are extremely useful as a practical production method of 3',3'-cGAMP.

DESCRIPTION OF EMBODIMENTS

The following is a detailed description of embodiments of the present invention. In order to avoid the complication of repetition, explanations of similar contents will be omitted as appropriate.

(1) Definition of Activity

A 3',3'-cGAMP synthase has an activity to catalyze reaction to produce 3',3'-cGAMP from one ATP molecule and one GTP molecule in the presence of both GTP and ATP. In the present invention, this activity is referred to as "3',3'-cGAMP synthesis activity."

In addition, the synthase has the activity to catalyze the reaction to produce c-di-GMP from two GTP molecules and c-di-AMP from two ATP molecules. Therefore, c-di-GMP or c-di-AMP is produced as a by-product even in the presence of both GTP and ATP. The activity to produce c-di-GMP as a by-product is called "c-di-GMP by-production activity", and the activity to produce c-di-AMP as a by-product is called "c-di-AMP by-production activity.

Regarding the 3',3'-cGAMP synthase, the ratio (%) of c-di-GMP by-production activity (specific activity) to 3',3'-cGAMP synthesis activity (specific activity) is called "c-di-GMP by-production ratio (%)" and the ratio (%) of c-di-AMP by-production activity (specific activity) to 3',3'-cGAMP synthesis activity (specific activity) is called "c-di-AMP by-production ratio (%)".

In the present invention, activity measurement is performed using an enzyme solution prepared by usual methods.

The reaction is carried out by adding the enzyme solution to a 50 mM Tris-HCl buffer solution (pH 8.0) containing 20 mM magnesium chloride, 1 mM GTP, and 1 mM ATP, and keeping the solution at 37° C. for 30 minutes. The reaction is then stopped by heat treatment at 100° C. for 30 seconds.

In the activity measurement of the present invention, the amount of 3',3'-cGAMP, c-di-GMP, c-di-AMP, etc., contained in the reaction solution obtained by the above method is quantified using known methods such as HPLC.

HPLC conditions are as follows. YMC™ Hydrosphere C18 (particle size: 5 μm, inner diameter: 4.6 mm, and length: 150 mm) is used as the column. 0.1 M triethylamine phosphate buffer (pH 6.0)+5% acetonitrile is used as mobile phase, flow rate is 0.6 mL/min, and mobile phase temperature is room temperature. For detection, 10 μL of a sample of the above reaction solution diluted 10 times with the mobile phase is provided to the column, and absorbance thereof is measured at 260 nm.

Under the above measurement conditions, retention times of 3',3'-cGAMP, c-di-GMP and c-di AMP are 25.0 min, 16.9 min and 40.5 min, respectively.

(2) Wild-Type 3',3'-cGAMP Synthase

In the present invention, "wild-type 3',3'-cGAMP synthase" means a 3',3'-cGAMP synthase that falls under at least one of the following (a) to (c) and does not have "by-production reducing mutation" described below:

(a) a protein containing amino acid sequence of SEQ ID: 1;
    (b) a protein containing an amino acid sequence having 90% or more identity to the amino acid sequence of SEQ ID: 1; and (c) a protein containing an amino acid sequence in which one to forty amino acids are deleted, substituted, inserted, or added in the amino acid sequence of SEQ ID: 1.

The 3',3'-cGAMP synthase listed in SEQ ID: 1 is Vc DncV encoded by a *Vibrio cholerae* 3',3'-cGAMP synthase gene (Vc dncv).

In the present application, "amino acid" is a generic term for organic compounds that have an amino group and a carboxyl group. It includes, for example, Ala, Arg, Asn, Asp, Cys, Gln, Glu, Gly, His, Ile, Leu, Lys, Met, Phe, Pro, Ser, Thr, Trp, Tyr, and Val, but are not limited thereto.

The wild-type 3',3'-cGAMP synthase in the present invention may be (a) the protein containing the amino acid sequence of SEQ ID: 1. An example of (a) the protein containing the amino acid sequence of SEQ ID: 1 includes a protein including a label sequence added for purification or other purposes to the extent that the 3',3'-cGAMP synthase activity is not lost.

The wild-type 3',3'-cGAMP synthase in the present invention may be (b) the protein containing the amino acid sequence having 90% or more identical to the amino acid sequence of SEQ ID: 1, as long as it does not have "by-production reducing mutation" or "high activity mutation."

The term "90% or more" used to describe the amino acid sequence identity of 3',3'-cGAMP synthase may be, for example, 90, 95, 98, 99, or 100%, may be any one of those values or more, or may be within any two of those values. The larger this value, the more desirable it is because the larger the value, the closer the property is considered to be to Vc DncV.

In the present application, the term "identity" is generally defined as percentage of the number of identical amino acids between two amino acid sequences or among three or more amino acid sequences, calculated according to methods known in the art. Before calculating the percentage, amino acid sequences in the groups of the amino acid sequences to be compared are aligned, and one or more gaps are introduced in some of the amino acid sequences if necessary, to maximize the percentage of identity. Methods for alignment, calculation of proportions, comparison methods, and computer programs related thereto are well known in the art (e.g., BLAST, GENETYX, etc.). In the present application, "homology" can be expressed as a value measured by BLAST of NCBI unless otherwise noted. When comparing amino acid sequences using BLAST, Blastp can be used as the default setting for the Algorithm. Measurement results are quantified as Positives or Identities.

The wild-type 3',3'-cGAMP synthase may be (c) the protein containing the amino acid sequence in which one to forty amino acids are deleted, substituted, inserted, or added in the amino acid sequence of SEQ ID: 1.

If one to forty amino acids in the wild-type 3',3'-cGAMP synthase are deleted, substituted, inserted, or added, it is preferable that the number of deletions, substitutions, insertions, or additions is either none or a few. This is because the fewer deletions or the like in the amino acid sequence are, the closer it will be to 3',3'-cGAMP synthase without any deletions or the like.

It is generally known that polypeptides having deletions, additions or insertions of one or more amino acid residues or substitutions of one or more amino acid residues with one or more other amino acids retain their biological activity (Mark et al., Proc Natl Acad Sci USA. 1984 September; 81(18):

5662-5666., Zoller et al., Nucleic Acids Res. 1982 Oct. 25; 10(20):6487-6500, Wang et al., Science. 1984 Jun. 29; 224(4656):1431-1433).

If one to forty amino acids of the wild-type 3',3'-cGAMP synthase are substituted with other amino acids, it is preferable that the amino acid is substituted with another amino acid having a conserved amino acid side chain property. The amino acid can be classified into, for example, hydrophobic amino acids (A, I, L, M, F, P, W, Y, and V), hydrophilic amino acids (R, D, N, C, E, Q, G, H, K, S, and T), amino acids with aliphatic side chains (G, A, V, L, I, and P), amino acids with hydroxyl-containing side chains (S, and T), amino acids with sulfur atom-containing side chains (C, and M), amino acids with carboxylic acid- and amide-containing side chains (D, N, E, and Q), amino acids with base-containing side chains (R, K, and H), and amino acids with aromatic side chains (H, F, Y, and W) (each letter in parentheses represents single letter of amino acid) according to the side chain property. Substitutions between amino acids in each of these groups are collectively referred to as "conservative substitutions."

(3) Mutant-Type 3',3'-cGAMP Synthases

Mutant-type 3',3'-cGAMP synthases are 3',3'-cGAMP synthases having one or more specific "by-production reducing mutations" in the amino acid sequence of the wild-type 3',3'-cGAMP synthase. The mutant-type 3',3'-cGAMP synthase may also have a "high activity mutation" as described below.

The "by-production reducing mutation" is explained below.

The "by-production reducing mutation" means one or more mutations that reduce the ratio of c-di-GMP by-production activity or c-di-AMP by-production activity to 3',3'-cGAMP synthetic activity when introduced into the wild-type 3',3'-cGAMP synthase.

The mutant-type 3',3'-cGAMP synthase with the "by-production reducing mutation" reduces the by-productions of c-di-GMP and c-di-AMP in the 3',3'-cGAMP synthesis reaction.

The terms " . . . by-production is reduced" and "reduce . . . by-production" specifically means that the ratio of c-di-GMP by-production activity (specific activity) to 3',3'-cGAMP synthesis activity (specific activity) (c-di-GMP by-production ratio) or the ratio of c-di-AMP by-production activity (specific activity) to 3',3'-cGAMP synthesis activity (specific activity) (c-di-AMP by-production ratio) as measured by the activity measurement method described above is 0.8 times or less than c-di-GMP by-production ratio or c-di-AMP by-production ratio of Vc DncV encoded in SEQ ID: 2, obtained by methods described in Working Examples 1 to 3.

The by-production reducing mutation includes one or more amino acid mutations selected from the group consisting of the following amino acid residues: Y117, N121, M130, K177, A292 and K350.

In the above notation, the number represents position in the amino acid sequence of the wild-type 3',3'-cGAMP synthase shown in SEQ ID: 1, and the letter to the left of the number represents the amino acid residue (single letter notation) at that position in the amino acid sequence of the wild-type 3',3'-cGAMP synthase shown in SEQ ID: 1.

In the above mutation, substituted amino acid residues can be any amino acid residue other than the original one, as long as the by-productions of c-di-GMP and c-di-AMP are suppressed.

Among the by-production reducing mutations shown above, it is preferable to include one or more mutations selected from the group consisting of the following mutations.

In the following notation, the numbers and letters to the left are as described above, but the letters in parentheses to the right of the numbers indicate the amino acid residues after mutation (single letter notation). For example, Y117 (H, R, or K) means a mutation that Tyr residue at position 117 in the amino acid sequence of the wild-type 3',3'-cGAMP synthase is replaced with one of the amino acid residues His, Arg and Lys.

When there is a mutation in Y117, the mutation is preferably Y117(H, R, or K), more preferably Y117(H). The reason why the above mutation is preferred is not certain, but it is thought that the substitution of Y117 with any one of the amino acids having the base-containing side chains (R, K, or H) changes substrate specificity.

When there is a mutation in N121, the mutation is preferably N121(I, G, A, V, L, or P), more preferably N121(I). The reason why the above mutation is preferred is not certain, but it is thought that the substitution of N121 with any one of the amino acids with the aliphatic side chains (I, G, A, V, L, or P) changes substrate specificity.

When there is a mutation in M130, the mutation is preferably M130 (V, I, G, A, L, P, F, H, Y, or W), more preferably M130 (V, or F). The reason why the above mutation is preferred is not certain, but it is thought that the substitution of M130 with either any one of the amino acids with the aliphatic side chains (G, A, V, L, I, or P) or any one of the amino acids with the aromatic-containing side chains (H, F, Y, or W) changes substrate specificity.

When there is a mutation in K177, the mutation is preferably K177(M, H, C, F, Y, or W), more preferably K177(M, H, or C). The reason why the above mutation is preferred is not certain, but it is thought that the substitution of K177 with either any one of the amino acids with the sulfur atom-containing side chains (C, or M) or any one of the amino acids with the aromatic-containing side chains (H, F, Y, or W) changes substrate specificity.

When there is a mutation in A292, the mutation is preferably A292(T, K, Y, S, F, W, R, or H), more preferably A292(T, K, or Y). The reason why the above mutation is preferred is not clear, but it is thought that the substitution of A292 with any one of the amino acids with the hydroxyl-containing side chains (S, or T), base-containing side chains (R, K, or H), or aromatic-containing side chains (H, F, Y, or W) changes substrate specificity.

When there is a mutation in K350, the mutation is preferably K350 (E, D, M, N, Q, or C), more preferably K350 (E, D, or M). The reason why the above mutation is preferred is not certain, but it is thought that the substitution of K350 with either any one of the amino acids with the sulfur atom-containing side chains (C, or M) or the amino acids with the carboxylic acids and amide-containing side chains (D, N, E, or Q) changes substrate specificity.

(4) High Activity Mutation

The mutant-type 3',3'-cGAMP synthase may have a "high activity mutation".

The "highly active mutation" is explained below.

In the mutant-type 3',3'-cGAMP synthase with the "high activity mutation", 3',3'-cGAMP synthesis activity (specific activity) is enhanced.

The terms " . . . activity is enhanced" and "enhance . . . activity" specifically means that the 3',3'-cGAMP synthesis activity (specific activity), as measured by the activity measurement method described above, is at least 1.2 times higher (e.g., may be 1.2, 1.5, 1.8, 2.0, 3.0, 5.0, or 10.0 times higher, may be any one of those values or more, or may be within any two of those values) before and after the introduction of the "high activity mutation."

The high activity mutation specifically includes one or more amino acid mutations selected from the group consisting of the following amino acid residues. In other words, the "high activity mutation" may be any one of amino acid mutations selected from the group consisting of the following amino acid residues or a combination of two or more amino acid mutations selected from the group consisting of the following amino acid residues.

R44, E146, H170, L211, E342 and S346.

Among the high activity mutations shown above, it is preferable to include one or more mutations selected from the group consisting of the following mutations.

R44H, E146D, H170P, L211P, E342K and S346P.

From the viewpoint of enhancing 3',3'-cGAMP synthesis activity, the mutation includes preferably E146D among them, more preferably E146D in combination with L413P, but is not limited to the combination of these mutations.

The L413P mutation alone does not enhance 3',3'-cGAMP synthesis activity, but it enhances 3',3'-cGAMP synthesis activity in combination with the E146D mutation.

In the above notation, numbers and letters on the left and right are as described above.

When combining the by-production reducing mutation with the high activity mutation in the present invention, any combination of the mutations is possible, but from the viewpoint of both by-production reducing and high activity, the combination is preferably four mutations of E146D, L413P, K177M and N121I, more preferably ten mutations of E146D, L413P, R44H, H170P, L211P, K177M, N121I, M130V, A292T and K350E.

(5) Production of Mutant-Type 3',3'-cGAMP Synthase

The mutant-type 3',3'-cGAMP synthase can be used as a purified enzyme solution or crude enzyme solution based on the expression of a gene encoding the mutant-type 3',3'-cGAMP synthase in microorganisms such as *Escherichia coli* having the gene.

The mutant-type 3',3'-cGAMP synthase gene is obtained by introducing the by-production reducing mutation into a wild-type 3',3'-cGAMP synthase gene. The wild-type 3',3'-cGAMP synthase gene can be obtained by cloning or chemical synthesis from organisms having the gene. Known methods of genetic modification (e.g., Nucleic Acids Res. 2004 Aug. 10; 32(14):e115) can be used.

Treated product of microorganism bodies as a crude enzyme solution or an enzyme obtained from the treated product as a purified enzyme can be used as examples. Preparation of microbial organism can be carried out by using a medium in which the microorganism can grow, culturing the microbial organism according to usual methods, and then collecting the cultured microbial organism by centrifugation or the like. Specifically, for example, bouillon medium, LB medium (1.0% tryptone, 0.5% yeast extract, 0.5% salt), 2×YT medium (1.6% tryptone, 1.0% yeast extract, 0.5% salt) or the like can be used as a medium, when bacteria belonging to the *Escherichia coli* group is used. After inoculating seed bacteria into the medium, the medium is cultured at 30 to 50° C. for 1 to 100 hours with stirring as necessary, and the resulting culture medium is centrifuged to recover the microorganism bodies.

As the crude enzyme solution, the above-mentioned microorganism bodies are treated according to general treatment methods such as mechanical rupture (by a waring blender, French press, homogenizer, mortar or the like), freezing-thawing, self-digestion, drying (by freeze-drying, air-drying or the like), enzyme treatment (by lysozyme or the like), ultrasonic treatment, chemical treatment (by acid, alkali treatment or the like). Supernatant obtained by centrifuging crushed microorganism bodies can be used as an example.

As the purified enzyme, those obtained by ordinary enzyme purification methods (salting out, isoelectric point precipitation, organic solvent precipitation, dialysis, various chromatographic treatments, or the like) to fractions having desired enzyme activity from the treated microorganism bodies can be used as an example.

(6) Synthesis of 3',3'-cGAMP Using Mutant-Type 3',3'-cGAMP Synthase

In the synthesis system of 3',3'-cGAMP, ATP and GTP are used as raw materials, and 3',3'-cGAMP synthase according to the embodiment of the invention is added as an enzyme. As the additive amount, ATP and GTP are in the range of 0.1 to 100 mM, preferably 0.1 to 20 mM, and the above 3',3'-cGAMP synthase is preferably in the range of 0.001 to 50 units/mL, but is not limited thereto. The molar ratio of each substrate is preferably ATP:GTP=1:1 usually, but may be changed to any substrate ratio. In addition, magnesium salt, manganese salt or the like may be added as metal salts to the reaction system. Magnesium chloride, manganese chloride or the like can be used as specific examples of metal salts. 3',3'-cGAMP can be synthesized by performing the reaction system at 15° C. or higher, preferably 30 to 50° C. for 0.5 to 100 hours, with stirring if necessary.

(7) Others

One of the embodiments of the present invention is a material for producing 3',3'-cGAMP, including 3',3'-cGAMP synthase according to the embodiment of the present invention. This material for producing 3',3'-cGAMP may include, for example, an aqueous solution or sol including 3',3'-cGAMP synthase according to the embodiment of the present invention.

One of the embodiments of the present invention is a polynucleotide encoding 3',3'-cGAMP synthase according to the embodiment of the present invention. Also, one of the embodiments of the present invention is a vector containing the polynucleotide. One of the embodiments of the present invention is a transformant including the polynucleotide or vector. The polynucleotide, vector, or transformant can be used to produce 3',3'-cGAMP synthase according to the embodiment of the present invention. The transformant includes a cell and an organism.

When the 3',3'-cGAMP synthase according to the embodiment of the present invention contains a specific amino acid sequence, any of the amino acids in the amino acid sequence may be chemically modified. Even in such a case, the 3',3'-cGAMP synthase of the present invention can contain the specific amino acid sequence. In general, in vivo chemical modifications to amino acids in proteins include N-terminal modifications (e.g., acetylation and myristoylation), C-terminal modifications (e.g., amidation and glycosylphosphatidylinositol addition), or side chain modifications (e.g., phosphorylation and glycosylation).

The term "polynucleotide" as used herein includes nucleotides, bases, and their equivalents, which are composed of a plurality of bound forms. The nucleotides and bases include DNA bases and RNA bases. The above equivalents include, for example, DNA bases and RNA bases that have undergone chemical modification, such as methylation and nucleotide analogs. The nucleotide analogs include non-naturally occurring nucleotides.

The term "DNA strand" refers to a form in which two or more DNA bases or their equivalents are linked together.

The term "RNA strand" refers to a form in which two or more RNA bases or their equivalents are linked together.

The term "nucleotide sequence" refer to a sequence of nucleotides or their equivalents that constitutes a polynucleotide. In general, the nucleotide sequence can be represented by A (adenine), G (guanine), C (cytosine), and T (thymine). T is interchangeable with U (uracil) according to the application. When the polynucleotide contains a specific base sequence containing two or more bases selected from group consisting of A, G, C, T and U, any of the bases in the sequence may be replaced by its equivalents. Even in such a case, the polynucleotide can contain the above specific base sequence. The polynucleotide can be synthesized using a DNA/RNA synthesizer. Alternatively, they can be purchased from a DNA base or RNA base synthesis contractor (e.g., Invitrogen, Takara Bio, etc.).

In the present application, the term "vector" can include, for example, E. coli-derived plasmids (e.g., pBR322, pUC12, and pET-Blue-2), Bacillus subtilis-derived plasmids (e.g., pUB110, and pTP5), yeast-derived plasmids (e.g., pSH19, and pSH15), animal cell expression plasmids (e.g., pA1-11, and pcDNAI/Neo), bacteriophages such as X phage, and virus vectors such as adenovirus, retrovirus, and baculovirus. These vectors can contain promoters, components necessary for protein expression, such as promoters, origin of replication, and antibiotic resistance genes. The vectors may be expression vectors.

In the above, the embodiments of the invention are described. However, these embodiments are exemplifications of the present invention. Various configurations other than the above may be employed. Also, the configurations described in the above embodiments can be adopted in combination.

EXAMPLES

Working Example 1

Construction of Wild-Type Vc dncv Gene Expression Plasmid pETBlue2-Km-DncV

The construction method of pETBlue2-Km-DncV is as follows. A plasmid pUCFa-Vc DncV was created by artificially synthesizing 3',3'-cGAMP synthase gene derived from Vibrio cholerae (Vc dncv) and inserting it into pUCFa. In the Vc dncv gene, a nucleotide sequence corresponding to the second amino acid residue (R) is AGA, but in the artificially synthesized gene, a mutation (R2G) was introduced in the second amino acid residue in order to add a recognition sequence for the restriction enzyme NcoI to the 5' end and set the sequence to GGA. During the artificial synthesis, the sequence was optimized for expression in E. coli as shown in SEQ ID: 2. In the following working examples, the optimized sequence is referred to as a wild-type Vc dncv gene, and the 3',3'-cGAMP synthase obtained from the gene sequence is referred to as a wild-type DncV. The plasmid was cut with restriction enzymes NcoI and BamHI. A plasmid pET-Blue-2-Km was digested with restriction enzymes NcoI and BamHI. The two DNA fragments were linked with T4 DNA ligase and introduced into a cytidine deoxycytidine deaminase (cdd) gene deficient strain (JM109Δcdd) of Escherichia coli strain JM109. A plasmid pETBlue2-Km-DncV was isolated from the obtained kanamycin-resistant transformants. pET-Blue-2-Km was constructed based on pET-Blue-2 (obtained from Novagen) and the expression plasmid pTrc 12-6 (JP2001-103973A), in which β-lactamase gene of pET-Blue-2 was completely deleted and the kanamycin resistance gene derived from Tn903 was inserted in the deletion site.

Working Example 2

Construction of Mutant-Type Vc dncv Gene Expression Plasmid

In the production of a mutant-type Vc dncv gene, SOE-PCR (Gene. 1989 Apr. 15; 77(1):51-9.) technique was used in both cases. Specifically, after obtaining two fragments by PCR using primers (sequence F) and (sequences r-1 to 21) and primers (sequence R) and (sequences f-1 to 21), the two fragments were used as templates for PCR using the corresponding primers (sequence F) and (sequence R). PCR using the corresponding primers (sequence F) and (sequence R) was performed using the two fragments as templates to obtain the mutant-type Vc dncv gene fragments. The relationship between each mutation and each primer is shown in Table 1. The underlined sequences in the table correspond to the amino acid residues into which the mutations are introduced.

TABLE 1

| SEQ ID | Name | Sequence (5'→3') | Mutation |
|---|---|---|---|
| 3 | F | ATGGGAATGACCTGGAACTTCCACCAGTAT | |
| 4 | R | TTAACCGCTAACCATTGTGCTCGAAATCTT | |
| 5 | f-1 | TTTCCAGCACGATACCCTCAATCGGCCGTTTCAACCGGGG | Y117H |
| 6 | r-1 | GGGTATCGTGCTGGAAAGAACCCTGTGTCCAGAAACGTGG | |
| 7 | f-2 | TACCCTCATTCGGCCGTTTCAACCGGGGCAGGAAATGGAC | N121I |
| 8 | r-2 | ACGGCCGAATGAGGGTATCGTACTGGAAAGAACCCTGTGT | |
| 9 | f-3 | GCAGGAAGTGGACATTGACGATGGCACTTACATGCCAATG | M130V |
| 10 | r-3 | CAATGTCCACTTCCTGCCCCGGTTGAAACGGCCGATTGAG | |
| 11 | f-4 | GCAGGAATTCGACATTGACGATGGCACTTACATGCCAATG | M130F |
| 12 | r-4 | CAATGTCGAATTCCTGCCCCGGTTGAAACGGCCGATTGAG | |
| 13 | f-5 | TGAGGCCATGCAGACTTGTGGCCGTATCAAAATTGAAGCA | K177M |

TABLE 1-continued

| SEQ ID | Name | Sequence (5'→3') | Mutation |
|--------|------|------------------|----------|
| 14 | r-5 | AAGTCTGCATGGCCTCAAATTTCCAGCCATGATTCTCTGC | |
| 15 | f-6 | TGAGGCCCATCAGACTTGTGGCCGTATCAAAATTGAAGCA | K177H |
| 16 | r-6 | AAGTCTGATGGGCCTCAAATTTCCAGCCATGATTCTCTGC | |
| 17 | f-7 | TGAGGCCTGCCAGACTTGTGGCCGTATCAAAATTGAAGCA | K177C |
| 18 | r-7 | AAGTCTGGCAGGCCTCAAATTTCCAGCCATGATTCTCTGC | |
| 19 | f-8 | GCGTGATACACAATGGGATGTTGGTGGTCCCAGCAGTATT | A292T |
| 20 | r-8 | CCCATTGTGTATCACGCCACGCTTTCATGAAGCGGCAGAC | |
| 21 | f-9 | GCGTGATAAGCAATGGGATGTTGGTGGTCCCAGCAGTATT | A292K |
| 22 | r-9 | CCCATTGCTTATCACGCCACGCTTTCATGAAGCGGCAGAC | |
| 23 | f-10 | GCGTGATTACCAATGGGATGTTGGTGGTCCCAGCAGTATT | A292Y |
| 24 | r-10 | CCCATTGGTAATCACGCCACGCTTTCATGAAGCGGCAGAC | |
| 25 | f-11 | CGATGAGGAACCTTTGTTTCCACCGTCATACAAACATGGG | K350E |
| 26 | r-11 | ACAAAGGTTCCTCATCGGTTGAGTCCGGCGACTCTACTCC | |
| 27 | f-12 | CGATGAGGACCCTTTGTTTCCACCGTCATACAAACATGGG | K350D |
| 28 | r-12 | ACAAAGGGTCCTCATCGGTTGAGTCCGGCGACTCTACTCC | |
| 29 | f-13 | CGATGAGATGCCTTTGTTTCCACCGTCATACAAACATGGG | K350M |
| 30 | r-13 | ACAAAGGCATCTCATCGGTTGAGTCCGGCGACTCTACTCC | |
| 31 | f-14 | GCGCACTCACGATGTGTTTGAAGAAGCCAAGGGCATTGCG | R44H |
| 32 | r-14 | ACACATCGTGAGTGCGCAAGCGAATGATTTTGCGAAGTGC | |
| 33 | f-15 | AGAGAATCCTGGCTGGAAATTTGAGGCCAAGCAGACTTGT | H170P |
| 34 | r-15 | TCCAGCCAGGATTCTCTGCAACCAGAGATTTCAGAGAGGC | |
| 35 | f-16 | GATTGCCCCCGAAGCGAACCGTAGCTTCGTTAAAGGCGCG | L211P |
| 36 | r-16 | TCGCTTCGGGGGCAATCTGTTTCTTCTGAAATTCATCTTT | |
| 37 | f-17 | TGGAGTAAAGTCGCCGGACTCAACCGATGAGAAACCTTTG | E342K |
| 38 | r-17 | CCGGCGACTTTACTCCACGCGCAAATTCCGACGGAAGATG | |
| 39 | f-18 | GCCGGACCCAACCGATGAGAAACCTTTGTTTCCACCGTCA | S346P |
| 40 | r-18 | CATCGGTTGGGTCCGGCGACTCTACTCCACGCGCAAATTC | |
| 41 | f-19 | AGTCTGATCCGAAAATTGGACATAGTCTGCTGATTCTGCT | E146D |
| 42 | r-19 | AATTTTCGGATCAGACTCGAAGATCGGCATTGGCATGTAA | |
| 43 | f-20 | AAAGCCCCGCCGGCATTTGCCCAAGAGCCGAGTAGTGCTT | L413P |
| 44 | r-20 | AATGCCGGCGGGGCTTTCGCCAGCACAATCAGTTCGCTGT | |

Each of the obtained DNA fragments was inserted into pETBlue2-Km with the IN-FUSION® HD Cloning Kit (Clontech) and introduced into JM109Acdd. Mutant-type Vc dncv gene expression plasmids were isolated from the obtained kanamycin-resistant transformants. The plasmid in which each mutation was introduced was named pETBlue2-Km-DncV plus the respective mutations. For example, the mutant-type Vc dncv gene expression plasmid encoding the mutant-type Vc DncV with K177M mutation was named pETBlue2-Km-DncV K177M. Then, using, as a template, the mutant-type Vc dncv gene expression plasmid which were obtained, mutant-type Vc dncv gene expression plasmid with multiple mutations were produced by introducing additional mutation by the same procedure, which were named in the same way. For example, by using pETBlue2-Km-DncV K177M as a template a plasmid with triple mutation was obtained by further introducing E146D and L413P mutations, which was named pETBlue2-Km-DncV K177M/E146D/L413P. Since the nucleotide sequence corresponding to the second amino acid residue in pETBlue2-Km-DncV was substituted, the same substitution was introduced in the mutant-type Vc dncv gene expression plasmid.

Working Example 3

Preparation of Wild-Type and Mutant-Type DncV
(1) Preparation of DncV Enzyme Solution

*E. coli* Tuner (DE3) pLacI strains carrying each of the
above wild-type or various mutant-type Vc dncv gene
expression plasmids were inoculated into 5 ml of LB medi-
ums (1.0% (w/v) peptone, 0.5% (w/v) yeast extract, 0.5%
(w/v) NaCl) containing 25 μg/mL of kanamycin. The inocu-
lated cells were incubated at 37° C. for 16 hours with
shaking. When the OD600 reached 3.5, IPTG was added to
a final concentration of 0.5 mM, the culture medium was
cooled to 25° C., and shaking was continued overnight. After
the end of incubation, the microorganism bodies were col-
lected by centrifugation (7,000×g, 10 min), suspended in 10
ml of buffer solutions (50 mM tris-hydrochloric acid (pH
7.5), 1 mM dithiothreitol), and then sonicated to break up the
microorganism bodies. The microorganism residues were
further removed by centrifugation (12,000×g, 10 min), and
the resulting supernatants were used as cell-free extract.
(2) Purification of DncV Each of the obtained cell-free extracts was applied to
HITRAP® Q FF (GE Healthcare), which was previously
equilibrated with buffer (50 mM Tris HCl (pH 7.5), 1 mM
dithiothreitol), and eluted with elution buffer (50 mM Tris
HCl (pH 7.5), 1 mM dithiothreitol, 1M NaCl) by gradient
elution to obtain active fractions. The fractions were applied
to PD-10 (GE Healthcare), which was previously equili-
brated with buffer (10 mM sodium phosphate (pH 7.5), 1
mM dithiothreitol), and the buffer was exchanged. Each
enzyme solution was applied to HITRAP® Heparin HP (GE
Healthcare), which was previously equilibrated with buffer
(10 mM sodium phosphate (pH 7.5), 1 mM dithiothreitol),
and eluted with elution buffer (10 mM sodium phosphate
(pH 7.5), 1 mM dithiothreitol, 1 M NaCl) by gradient elution
to obtain active fractions. Each fraction was applied to
PD-10 (GE Healthcare), which was previously equilibrated
with buffer (50 mM Tris HCl (pH 7.5), 1 mM dithiothreitol,
150 mM NaCl), and the buffer was exchanged. Each enzyme
solution was used as purified Vc DncV for subsequent
experiments.

Working Example 4

Evaluation of Activity of Wild-Type and Mutant-Type DncV

Each of the 3',3'-cGAMP synthesis activities of purified
Vc DncVs obtained in Working Example 3 was measured by
the following method. In addition, the synthetic activities of
c-di-GMP and c-di-AMP, which were by-products of the
reaction, were measured and calculated. In other words, each
of the above purified enzyme solutions was added to a 50
mM Tris-HCl buffer solution (pH 8.0) containing 20 mM
magnesium chloride, 1 mM GTP, and 1 mM ATP, main-
tained at 37° C. for 30 minutes, and then the reaction was
stopped by heat treatment at 100° C. for 30 seconds.

HPLC was used to quantify 3',3'-cGAMP and linear
intermediate pppApG, as well as the by-product c-di-GMP/
c-di-AMP and linear intermediate pppGpG/pppApA.

The HPLC conditions were as follows. YMC™ Hydro-
sphere C18 (particle size 5 μm, inner diameter 4.6 mm,
length 150 mm) was used as a column. As mobile phase, 0.1
M triethylamine phosphate buffer (pH 6.0)+5% acetonitrile
was used, flow rate was 0.6 mL/min, and mobile phase
temperature was room temperature. For detection, 10 μL of
sample of each of the above reaction solutions diluted 10
times with the mobile phase was provided to the column,
and the absorption at a wavelength of 260 nm was measured.

Under the above measurement conditions, 3',3'-cGAMP
has 25.0 min of the retention time, pppApG has 19.7 min of
the retention time, c-di-GMP has 16.9 min of the retention
time, pppGpG has 12.6 min of the retention time, c-di-AMP
has 40.5 min of the retention time, and pppApA has 32.4 min
of the retention time.

A specific activity was calculated as one unit which is an
activity to generate 1 μmol of linear intermediates and the
corresponding cyclic dinucleotides per minute at 37° C.

The results are shown in Table 2.

In the table, "(A) 3',3'-cGAMP (U/mg)" is the specific
activity of 3',3'-cGAMP synthetic activity, "(B) c-di-GMP
(U/mg)" is the specific activity of c-di-GMP by-production
activity, "(C) c-di-AMP (U/mg)" is the specific activity of
c-di-AMP by-production activity, "ratio of (B)/(A)" is the
ratio of c-di-GMP by-production activity of each mutant
strain to the c-di-GMP by-production activity of wild-type
DncV (Comparative Example 1), and "(C)/(A)" is the ratio
of the ratio of c-di-AMP by-production activity of each
mutant strain to the ratio of c-di-AMP by-production activity
to wild-type DncV.

The mutant strains having one by-production reducing
mutation are designated as Examples 1-1 to 1-13, the mutant
strains having one activity-enhancing mutation and one
by-production reducing mutation are designated as
Examples 2-1 to 2-5, the mutant strains having an activity-
enhancing mutation (E146D/L413P combination) and one
by-production reducing mutation are designated as
Examples 3-1 to 3-6, and the mutant strains having multiple
by-product reduction and activity-enhancing mutations are
designated as Examples 4-1 to 4-2. The artificial synthetic
DncV encoded by SEQ ID: 2 is designated as Comparative
Example 1, and the mutant strain having only the activity-
enhancing mutation (combination of E146D/L413P) is des-
ignated as Comparative Example 2.

In addition, if the c-di-GMP by-production ratio or c-di-
AMP by-production ratio in the mutant-type 3',3'-cGAMP
synthase is 0.8 times or less than the c-di-GMP by-produc-
tion ratio or c-di-AMP by-production ratio to wild-type
(artificially synthesized DncV) 3',3'-cGAMP synthase, the
ratios are indicated by filling in the table.

TABLE 2

| | Purified enzyme activity analysis (1 mM ATP/GTP) | (A)cGAMP (U/mg) | (B)cdGMP (U/mg) | (C)cdAMP (U/mg) | (B)/(A) | (C)/(A) |
|---|---|---|---|---|---|---|
| Comparative Example 1 | Wild Type | 0.9616 | 0.0456 | 0.0778 | — | — |
| Example 1-1 | Y117H | 0.1403 | 0.0067 | 0.0060 | 1.01 | 0.53 |
| Example 1-2 | N121I | 0.8493 | 0.0325 | 0.0291 | 0.81 | 0.42 |
| Example 1-3 | M130V | 0.1932 | 0.0071 | 0.0070 | 0.78 | 0.45 |

TABLE 2-continued

| | Purified enzyme activity analysis (1 mM ATP/GTP) | (A)cGAMP (U/mg) | (B)cdGMP (U/mg) | (C)cdAMP (U/mg) | (B)/(A) | (C)/(A) |
|---|---|---|---|---|---|---|
| Example 1-4 | M130F | 0.1809 | 0.0044 | 0.0034 | 0.51 | 0.23 |
| Example 1-5 | K177M | 0.2401 | 0.0082 | 0.0028 | 0.72 | 0.14 |
| Example 1-6 | K177H | 0.1570 | 0.0062 | 0.0018 | 0.83 | 0.15 |
| Example 1-7 | K177C | 0.1259 | 0.0073 | 0.0024 | 1.23 | 0.24 |
| Example 1-8 | A292T | 0.1072 | 0.0042 | 0.0031 | 0.83 | 0.36 |
| Example 1-9 | A292K | 0.0616 | 0.0023 | 0.0027 | 0.78 | 0.53 |
| Example 1-10 | A292Y | 0.0477 | 0.0029 | 0.0014 | 1.27 | 0.36 |
| Example 1-11 | K350E | 0.8097 | 0.0330 | 0.0325 | 0.86 | 0.50 |
| Example 1-12 | K350D | 0.6499 | 0.0254 | 0.0262 | 0.82 | 0.50 |
| Example 1-13 | K350M | 0.9103 | 0.0292 | 0.0545 | 0.68 | 0.74 |
| Example 2-1 | R44H/K177M | 0.3035 | 0.0068 | 0.0037 | 0.47 | 0.15 |
| Example 2-2 | H170P/K177M | 0.4000 | 0.0128 | 0.0090 | 0.68 | 0.28 |
| Example 2-3 | L211P/K177M | 0.4108 | 0.0113 | 0.0050 | 0.58 | 0.15 |
| Example 2-4 | S346P/K177M | 0.3904 | 0.0078 | 0.0067 | 0.42 | 0.21 |
| Example 2-5 | E342K/K177M | 0.6880 | 0.0215 | 0.0101 | 0.66 | 0.18 |
| Comparative Example 2 | E146D/L413P | 2.2817 | 0.1008 | 0.1811 | 0.93 | 0.98 |
| Example 3-1 | E146D/L413P/ Y117H | 0.9263 | 0.0260 | 0.0437 | 0.59 | 0.58 |
| Example 3-2 | E146D/L413P/ N121I | 2.3776 | 0.0859 | 0.0775 | 0.76 | 0.40 |
| Example 3-3 | E146D/L413P/ M130V | 1.6783 | 0.0596 | 0.0787 | 0.75 | 0.58 |
| Example 3-4 | E146D/L413P/ K177M | 1.7347 | 0.0556 | 0.0393 | 0.68 | 0.28 |
| Example 3-5 | E146D/L413P/ A292T | 1.9204 | 0.0661 | 0.0841 | 0.73 | 0.54 |
| Example 3-6 | E146D/L413P/ K350E | 2.8815 | 0.1033 | 0.1439 | 0.76 | 0.62 |
| Example 4-1 | E146D/L413P/ K177M/N121I | 0.8991 | 0.0294 | 0.0150 | 0.69 | 0.21 |
| Example 4-2 | E146D/L413P/ R44H/H170P/ L211P/K177M/ N121I/M130V/ A292T/K350E | 1.1831 | 0.0270 | ND | 0.48 | — |

From the above Table 2, it is clear that the c-di-GMP by-production ratio and c-di-AMP by-production ratio were decreased in the 3',3'-cGAMP synthase with mutations at Y117, N121, M130, K177, A292, and K350 positions.

Specifically, it was found that the by-products were reduced in Examples 1-1 to 1-13, Examples 2-1 to 2-5, Examples 3-1 to 3-6, and Examples 4-1 to 4-2 with the corresponding mutations.

In addition, it was found that the specific activity of 3',3'-cGAMP synthesis activity was enhanced in the mutant-type 3',3'-cGAMP synthases with activity-enhancing mutations (specifically, Examples 2-1 to 2-5, Comparative Example 2, Examples 3-1 to 3-6, and Examples 4-1 to 4-2).

Furthermore, it was found that, regarding the mutant-type 3',3'-cGAMP synthase, the 3',3'-cGAMP synthase with multiple by-product reduction and activity-enhancing mutations (specifically, Examples 4-1 to 4-2) exhibited higher by-product-reducing and/or activity-enhancing effects.

Working Example 5

Synthesis of 3',3'-cGAMP by Mutant-Type DncV

The purified Vc DncVs obtained in Working Example 3 were subjected to the 3',3'-cGAMP synthesis reaction as described below. In addition, it was examined whether 3',3'-cGAMP can be synthesized with the mutant-type 3',3'-cGAMP synthases of the present invention by quantifying the c-di-GMP and c-di-AMP by-products produced by the reaction.

That is, the reactions were carried out by adding each of the above purified enzyme solutions to 50 mM Tris-HCl buffer (pH 8.0) containing 10 (v/v) % glycerol, 20 mM magnesium chloride, 5 mM GTP, and 5 mM ATP, and keeping them warm at 30° C. for 21 hours, followed by heat treatment at 100° C. for 30 seconds to stop the reactions.

Based on the results of the activity measurement in Working Example 4, the amount of the purified enzyme to be added was 0.04 U/mL of 3',3'-cGAMP synthesis activity. The produced 3',3'-cGAMP and c-di-GMP/c-di-AMP by-products were quantified by HPLC. The results are shown in Table 3.

In the table,

"(a) 3',3'-cGAMP (mM)" is the produced concentration of 3',3'-cGAMP,

"(b) c-di-GMP (mM)" is the produced concentration of c-di-GMP,

"(c) c-di-AMP (mM)" is the produced concentration of c-di-AMP,

"(b)/(a) ratio" is the ratio of "the produced concentration of c-di-GMP divided by the produced concentration of 3',3'-cGAMP of each mutant strain" to "the produced concentration of c-di-GMP divided by the produced concentration of 3',3'-cGAMP synthesis activity of wild-type DncV (Comparative Example 3)", "(c)/(a)" is the ratio of "the produced concentration of c-di-AMP divided by the produced concentration of 3',3'-cGAMP by each mutant strain" to "the produced concentration of c-di-AMP divided by the produced concentration of 3',3'-cGAMP synthesis activity of wild-type DncV (Comparative Example 3)".

The mutant strains having one by-production reducing mutation are designated as Examples 5-1 to 5-5, the mutant strains having the activity-enhancing mutation (E146D/ L413P combination) and one by-production reducing mutation are designated as Examples 6-1 to 6-6, and the mutant strains having both the by-product reduction and activity-enhancing mutation are designated as Examples 7-1 to 7-2.

The artificial synthetic DncV encoded by SEQ ID: 2 is designated as Comparative Example 3, and the mutant strain having only the activity-enhancing mutation (combination of E146D/L413P) is designated as Comparative Example 4.

In addition, if "(b)/(a)" or "(c)/(a)" in the mutant-type 3',3'-cGAMP synthase is 0.8 times or less than "(b)/(a)" or "(c)/(a)" of the wild-type 3',3'-cGAMP synthase, the ratios are indicated by filling in the table.

TABLE 3

| | Purified enzyme activity analysis (5 mM ATP/GTP) | (a)cGAMP (mM) | (b)cdGMP (mM) | (c)cdAMP (mM) | (b)/(a) | (c)/(a) |
|---|---|---|---|---|---|---|
| Comparative Example 3 | Wild Type | 3.680 | 0.160 | 0.354 | — | — |
| Example 5-1 | Y117H | 3.695 | 0.150 | 0.193 | 0.93 | 0.54 |
| Example 5-2 | N121I | 3.639 | 0.113 | 0.177 | 0.71 | 0.51 |
| Example 5-3 | M130V | 3.836 | 0.124 | 0.216 | 0.74 | 0.59 |
| Example 5-4 | K177M | 3.905 | 0.105 | 0.150 | 0.62 | 0.4 |
| Example 5-5 | K350E | 3.717 | 0.131 | 0.240 | 0.81 | 0.67 |
| Comparative Example 4 | E146D, L413P | 3.657 | 0.158 | 0.350 | 0.99 | 0.99 |
| Example 6-1 | E146D, L413P, Y117H | 3.889 | 0.120 | 0.244 | 0.71 | 0.65 |
| Example 6-2 | E146D, L413P, N121I | 3.646 | 0.108 | 0.189 | 0.68 | 0.54 |
| Example 6-3 | E146D, L413P, M130V | 3.827 | 0.113 | 0.281 | 0.68 | 0.76 |
| Example 6-4 | E146D, L413P, K177M | 3.811 | 0.100 | 0.161 | 0.60 | 0.44 |
| Example 6-5 | E146D, L413P, A292T | 3.734 | 0.098 | 0.214 | 0.60 | 0.59 |
| Example 6-6 | E146D, L413P, K350E | 3.773 | 0.127 | 0.278 | 0.78 | 0.77 |
| Example 7-1 | E146D, L413P, K177M, N121I | 3.689 | 0.096 | 0.112 | 0.60 | 0.32 |
| Example 7-2 | E146D, L413P, R44H, H170P, L211P, K177M, N121I, M130V, A292T, K350E | 3.627 | 0.032 | 0.052 | 0.20 | 0.15 |

From the above Table 3, it was found that the mutant-type 3',3'-cGAMP synthase of the present invention can reduce the by-products of c-di-GMP and c-di-AMP even when used for practical 3',3'-cGAMP synthesis.

Specifically, it was found that the by-products were reduced in Examples 5-1 to 5-5, Examples 6-1 to 6-6, and Examples 7-1 to 7-2 with the corresponding mutations.

This indicates that the enzyme of the present invention and the method for synthesizing 3',3'-cGAMP using the enzyme are extremely useful as a practical method for producing 3',3'-cGAMP.

The present invention has been explained based on Examples. The person skilled in the art will understand that these examples are only illustrative, that various variations can be adapted and that such variations are also within the scope of the present invention.

What is claimed is:

1. A mutant-type 3',3'-cGAMP synthase comprising a by-production reducing mutation and a high activity mutation, wherein the by-production reducing mutation is one or more amino acid mutations selected from the group consisting of the following amino acid residues: Y117, N121, M130, K177, A292, and K350 of wild-type 3',3'-cGAMP synthase consisting of SEQ ID NO: 1, the high activity mutation is one or more amino acid mutations selected from the group consisting of the following amino acid residues: L211 and E342 of wild-type 3',3'-cGAMP synthase, the by-production reducing mutation contains at least one mutation selected from the group consisting of the following amino acid residues: Y117 (H, R, or K), N121 (I, G, A, V, L, or P), M130 (V, I, G, A, L, P, F, H, Y, or W), K177 (M, H, C, F, Y, or W), A292 (T, K, Y, S, F, W, R, or H), and K350 (E, D, M, N, Q, or C), and the mutant-type 3',3'-cGAMP synthase reduces by-productions of c-di-GMP and c-di-AMP in 3',3'-cGAMP synthesis reaction and enhances 3',3'-cGAMP synthesis activity in comparison with the wild-type 3',3'-cGAMP synthase consisting of SEQ ID NO: 1, the high activity mutation enhances the 3',3'-cGAMP synthesis activity, and the by-production reducing mutation reduces the by-productions of c-di-GMP and c-di-AMP.

2. The mutant-type 3',3'-cGAMP synthase according to claim 1, wherein the by-production reducing mutation contains at least one mutation selected from the group consisting of the following amino acid residues:
   Y117 (H),
   N121 (I),
   M130 (V, or F),
   K177 (M, H, or C),
   A292 (T, K, or Y), and
   K350 (E, D, or M).

3. A polynucleotide encoding the mutant-type 3',3'-cGAMP synthase according to claim 1.

4. An expression vector including the polynucleotide according to claim 3.

5. A transformant comprising the polynucleotide according to claim 3.

6. A method for producing 3',3'-cGAMP from one ATP molecule and one GTP molecule comprising contacting the mutant-type 3',3'-cGAMP synthase produced by culturing the transformant according to claim 5 with said one ATP molecule and one GTP molecule.

7. A transformant comprising the expression vector according to claim 4.

8. The mutant-type 3',3'-cGAMP synthase according to claim 1, wherein high activity mutation contains at least one mutation selected from the group consisting of the following amino acid residues:
   L211P, and
   E342K.

9. The mutant-type 3',3'-cGAMP synthase according to claim 8, wherein the by-production reducing mutation comprises the amino acid mutations: N121 I, M130V, K177M, A292T, and K350E of wild-type 3',3'-cGAMP synthase, and the high activity mutation further comprises at least one mutation selected from the group consisting of the following amino acid residues: R44H, E146D, and H170P and L211P of wild-type 3',3'-cGAMP synthase consisting of SEQ ID NO: 1.

10. The mutant-type 3',3'-cGAMP synthase according to claim 1, wherein the by-production reducing mutation contains N121 (I, G, A, V, L, or P) of wild-type 3',3'-cGAMP synthase consisting of SEQ ID NO: 1.

11. The mutant-type 3',3'-cGAMP synthase according to claim 10, wherein the by-production reducing mutation contains N121(I).

12. The mutant-type 3',3-cGAMP synthase according to claim 1, further comprising an amino acid mutation L413P of wild-type 3',3'-cGAMP synthase consisting of SEQ ID NO: 1.

13. A mutant-type 3',3'-cGAMP synthase comprising a by-production reducing mutation and a high activity mutation, wherein the by-production reducing mutation is one or more amino acid mutations selected from the group consisting of the following amino acid residues: Y117, N121, M130, K177, A292, and K350 of wild-type 3',3'-cGAMP synthase consisting of SEQ ID NO: 1, the high activity mutation is one or more amino acid mutations selected from the group consisting of the following amino acid residues: R44, E146, H170, L211, E342 and S346 of wild-type 3',3'-cGAMP synthase consisting of SEQ ID NO: 1, the by-production reducing mutation contains at least one mutation selected from the group consisting of the following amino acid residues: Y117 (H, R, or K), N121 (1, G, A, V, L, or P), M130 (V, I, G, A, L, P, F, H, Y, or W), K177 (M, H, C, F, Y, or W), A292 (T, K, Y, S, F, W, R, or H), and K350 (E, D, M, N, O, or C), and the mutant-type 3',3'-cGAMP synthase reduces by-productions of c-di-GMP and c-di-AMP in 3',3'-cGAMP synthesis reaction and enhances 3',3'-cGAMP synthesis activity in comparison with the wild-type 3',3'-cGAMP synthase consisting of SEQ ID NO: 1, the high activity mutation enhances the 3',3'-cGAMP synthesis activity, the by-production reducing mutation reduces the by-productions of c-di-GMP and c-di-AMP, and the high activity mutation contains at least one mutation selected from the group consisting of the following amino acid residues: R44H, E146D, H170P, L211P, E342K and S346P, and the mutant-type 3',3'-cGAMP synthase further comprises an amino acid mutation L413P of wild-type 3',3'-cGAMP synthase consisting of SEQ ID NO: 1.

14. The mutant-type 3',3'-cGAMP synthase according to claim 8, wherein the by-production reducing mutation comprises the amino acid mutations: N121 I, M130V, K177M, A292T, and K350E of wild-type 3',3'-cGAMP synthase consisting of SEQ ID NO: 1.

* * * * *

SEQUENCE LISTING

<160> NUMBER OF SEQ ID NOS: 46

<210> SEQ ID NO 1
<211> LENGTH: 436
<212> TYPE: PRT
<213> ORGANISM: Vibrio cholerae

<400> SEQUENCE: 1

Met Arg Met Thr Trp Asn Phe His Gln Tyr Tyr Thr Asn Arg Asn Asp
1               5                   10                  15

Gly Leu Met Gly Lys Leu Val Leu Thr Asp Glu Glu Lys Asn Asn Leu
            20                  25                  30

-continued

```
Lys Ala Leu Arg Lys Ile Ile Arg Leu Arg Thr Arg Asp Val Phe Glu
        35                  40                  45

Glu Ala Lys Gly Ile Ala Lys Ala Val Lys Lys Ser Ala Leu Thr Phe
        50                  55                  60

Glu Ile Ile Gln Glu Lys Val Ser Thr Thr Gln Ile Lys His Leu Ser
65                  70                  75                  80

Asp Ser Glu Gln Arg Glu Val Ala Lys Leu Ile Tyr Glu Met Asp Asp
                85                  90                  95

Asp Ala Arg Asp Glu Phe Leu Gly Leu Thr Pro Arg Phe Trp Thr Gln
                100                 105                 110

Gly Ser Phe Gln Tyr Asp Thr Leu Asn Arg Pro Phe Gln Pro Gly Gln
                115                 120                 125

Glu Met Asp Ile Asp Asp Gly Thr Tyr Met Pro Met Pro Ile Phe Glu
        130                 135                 140

Ser Glu Pro Lys Ile Gly His Ser Leu Leu Ile Leu Leu Val Asp Ala
145                 150                 155                 160

Ser Leu Lys Ser Leu Val Ala Glu Asn His Gly Trp Lys Phe Glu Ala
                165                 170                 175

Lys Gln Thr Cys Gly Arg Ile Lys Ile Glu Ala Glu Lys Thr His Ile
                180                 185                 190

Asp Val Pro Met Tyr Ala Ile Pro Lys Asp Glu Phe Gln Lys Lys Gln
        195                 200                 205

Ile Ala Leu Glu Ala Asn Arg Ser Phe Val Lys Gly Ala Ile Phe Glu
        210                 215                 220

Ser Tyr Val Ala Asp Ser Ile Thr Asp Asp Ser Glu Thr Tyr Glu Leu
225                 230                 235                 240

Asp Ser Glu Asn Val Asn Leu Ala Leu Arg Glu Gly Asp Arg Lys Trp
                245                 250                 255

Ile Asn Ser Asp Pro Lys Ile Val Glu Asp Trp Phe Asn Asp Ser Cys
                260                 265                 270

Ile Arg Ile Gly Lys His Leu Arg Lys Val Cys Arg Phe Met Lys Ala
        275                 280                 285

Trp Arg Asp Ala Gln Trp Asp Val Gly Gly Pro Ser Ser Ile Ser Leu
        290                 295                 300

Met Ala Ala Thr Val Asn Ile Leu Asp Ser Val Ala His Asp Ala Ser
305                 310                 315                 320

Asp Leu Gly Glu Thr Met Lys Ile Ile Ala Lys His Leu Pro Ser Glu
                325                 330                 335

Phe Ala Arg Gly Val Glu Ser Pro Asp Ser Thr Asp Glu Lys Pro Leu
                340                 345                 350

Phe Pro Pro Ser Tyr Lys His Gly Pro Arg Glu Met Asp Ile Met Ser
                355                 360                 365

Lys Leu Glu Arg Leu Pro Glu Ile Leu Ser Ser Ala Glu Ser Ala Asp
        370                 375                 380

Ser Lys Ser Glu Ala Leu Lys Lys Ile Asn Met Ala Phe Gly Asn Arg
385                 390                 395                 400

Val Thr Asn Ser Glu Leu Ile Val Leu Ala Lys Ala Leu Pro Ala Phe
                405                 410                 415

Ala Gln Glu Pro Ser Ser Ala Ser Lys Pro Glu Lys Ile Ser Ser Thr
                420                 425                 430

Met Val Ser Gly
        435
```

<210> SEQ ID NO 2
<211> LENGTH: 1311
<212> TYPE: DNA
<213> ORGANISM: Artificial Sequence
<220> FEATURE:
<223> OTHER INFORMATION: gene

<400> SEQUENCE: 2

```
atgggaatga cctggaactt ccaccagtat tacaccaatc gcaatgacgg tctgatgggc       60
aaactggtgc tgacagatga agaaaagaat aacctgaaag cacttcgcaa aatcattcgc      120
ttgcgcactc gcgatgtgtt tgaagaagcc aagggcattg cgaaagcggt caagaagtcc      180
gcacttacgt tcgaaatcat ccaggagaaa gtcagcacga cccaaatcaa acacttatcc      240
gactcagagc aacgtgaagt ggctaaactg atctatgaaa tggatgacga tgctcgtgac      300
gaatttctgg gtttgacccc acgtttctgg acacagggtt cttccagta cgataccctc      360 aatcggccgt ttcaaccggg gcaggaaatg gacattgacg atggcactta catgccaatg      420
ccgatcttcg agtctgaacc gaaaattgga catagtctgc tgattctgct tgtggatgcc      480
tctctgaaat ctctggttgc agagaatcat ggctggaaat ttgaggccaa gcagacttgt      540
ggccgtatca aaattgaagc agagaaaacc catatcgatg tgcccatgta tgccattccg      600
aaagatgaat ttcagaagaa acagattgcc ctcgaagcga accgtagctt cgttaaaggc      660
gcgatcttcg aatcctatgt ggcggatagc atcaccgacg atagcgaaac ctatgaactc      720
gatagtgaaa acgtaaatct ggccttacgc gaaggtgatc gcaaatggat taactcagac      780
ccgaaaattg tggaagattg gtttaacgac tcgtgcattc gcattggcaa acacttgcgc      840
aaagtctgcc gcttcatgaa agcgtggcgt gatgcacaat gggatgttgg tggtcccagc      900
agtattagct taatggctgc aacggttaac attctcgact ccgtagctca cgatgcgtca      960
gatctgggcg aaacgatgaa aatcattgcc aaacatcttc cgtcggaatt tgcgcgtgga     1020
gtagagtcgc cggactcaac cgatgagaaa cctttgtttc caccgtcata caaacatggg     1080
cctcgcgaaa tggatatcat gtccaaactg gaacggctgc ctgaaattct gtcgtctgct     1140
gaaagtgcgg acagcaaatc cgaggcgtta aagaagatca acatggcgtt tgggaatcgt     1200
gtcacgaaca gcgaactgat tgtgctggcg aaagccctgc cggcatttgc ccaagagccg     1260
agtagtgctt cgaaaccaga gaagatttcg agcacaatgg ttagcggtta a              1311
```

<210> SEQ ID NO 3
<211> LENGTH: 30
<212> TYPE: DNA
<213> ORGANISM: Artificial Sequence
<220> FEATURE:
<223> OTHER INFORMATION: primer

<400> SEQUENCE: 3

```
atgggaatga cctggaactt ccaccagtat                                         30
```

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4

```
ttaaccgcta accattgtgc tcgaaatctt                                         30
```

<210> SEQ ID NO 5

<211> LENGTH: 40
<212> TYPE: DNA
<213> ORGANISM: Artificial Sequence
<220> FEATURE:
<223> OTHER INFORMATION: primer

<400> SEQUENCE: 5
tttccagcac gataccctca atcggccgtt tcaaccgggg                    40

<210> SEQ ID NO 6
<211> LENGTH: 40
<212> TYPE: DNA
<213> ORGANISM: Artificial Sequence
<220> FEATURE:
<223> OTHER INFORMATION: primer

<400> SEQUENCE: 6
gggtatcgtg ctggaaagaa ccctgtgtcc agaaacgtgg                    40

<210> SEQ ID NO 7
<211> LENGTH: 40
<212> TYPE: DNA
<213> ORGANISM: Artificial Sequence
<220> FEATURE:
<223> OTHER INFORMATION: primer

<400> SEQUENCE: 7
tttccagacg gataccctca atcggccgtt tcaaccgggg                    40

<210> SEQ ID NO 8
<211> LENGTH: 40
<212> TYPE: DNA
<213> ORGANISM: Artificial Sequence
<220> FEATURE:
<223> OTHER INFORMATION: primer

<400> SEQUENCE: 8
gggtatccgt ctggaaagaa ccctgtgtcc agaaacgtgg                    40

<210> SEQ ID NO 9
<211> LENGTH: 40
<212> TYPE: DNA
<213> ORGANISM: Artificial Sequence
<220> FEATURE:
<223> OTHER INFORMATION: primer

<400> SEQUENCE: 9
taccctcatt cggccgtttc aaccggggca ggaaatggac                    40

<210> SEQ ID NO 10
<211> LENGTH: 40
<212> TYPE: DNA
<213> ORGANISM: Artificial Sequence
<220> FEATURE:
<223> OTHER INFORMATION: primer

<400> SEQUENCE: 10
acggccgaat gagggtatcg tactggaaag aaccctgtgt                    40

<210> SEQ ID NO 11
<211> LENGTH: 40
<212> TYPE: DNA
<213> ORGANISM: Artificial Sequence
<220> FEATURE:
<223> OTHER INFORMATION: primer

<400> SEQUENCE: 11

-continued gcaggaagtg gacattgacg atggcactta catgccaatg                    40

<210> SEQ ID NO 12
<211> LENGTH: 40
<212> TYPE: DNA
<213> ORGANISM: Artificial Sequence
<220> FEATURE:
<223> OTHER INFORMATION: primer

<400> SEQUENCE: 12
caatgtccac ttcctgcccc ggttgaaacg gccgattgag                    40

<210> SEQ ID NO 13
<211> LENGTH: 40
<212> TYPE: DNA
<213> ORGANISM: Artificial Sequence
<220> FEATURE:
<223> OTHER INFORMATION: primer

<400> SEQUENCE: 13
gcaggaattc gacattgacg atggcactta catgccaatg                    40

<210> SEQ ID NO 14
<211> LENGTH: 40
<212> TYPE: DNA
<213> ORGANISM: Artificial Sequence
<220> FEATURE:
<223> OTHER INFORMATION: primer

<400> SEQUENCE: 14
caatgtcgaa ttcctgcccc ggttgaaacg gccgattgag                    40

<210> SEQ ID NO 15
<211> LENGTH: 40
<212> TYPE: DNA
<213> ORGANISM: Artificial Sequence
<220> FEATURE:
<223> OTHER INFORMATION: primer

<400> SEQUENCE: 15
tgaggccatg cagacttgtg gccgtatcaa aattgaagca                    40

<210> SEQ ID NO 16
<211> LENGTH: 40
<212> TYPE: DNA
<213> ORGANISM: Artificial Sequence
<220> FEATURE:
<223> OTHER INFORMATION: primer

<400> SEQUENCE: 16
aagtctgcat ggcctcaaat ttccagccat gattctctgc                    40

<210> SEQ ID NO 17
<211> LENGTH: 40
<212> TYPE: DNA
<213> ORGANISM: Artificial Sequence
<220> FEATURE:
<223> OTHER INFORMATION: primer

<400> SEQUENCE: 17
tgaggcccat cagacttgtg gccgtatcaa aattgaagca                    40

<210> SEQ ID NO 18
<211> LENGTH: 40
<212> TYPE: DNA

-continued

<213> ORGANISM: Artificial Sequence
<220> FEATURE:
<223> OTHER INFORMATION: primer

<400> SEQUENCE: 18
aagtctgatg ggcctcaaat ttccagccat gattctctgc                              40

<210> SEQ ID NO 19
<211> LENGTH: 40
<212> TYPE: DNA
<213> ORGANISM: Artificial Sequence
<220> FEATURE:
<223> OTHER INFORMATION: primer

<400> SEQUENCE: 19
tgaggcctgc cagacttgtg gccgtatcaa aattgaagca                              40

<210> SEQ ID NO 20
<211> LENGTH: 40
<212> TYPE: DNA
<213> ORGANISM: Artificial Sequence
<220> FEATURE:
<223> OTHER INFORMATION: primer

<400> SEQUENCE: 20
aagtctggca ggcctcaaat ttccagccat gattctctgc                              40

<210> SEQ ID NO 21
<211> LENGTH: 40
<212> TYPE: DNA
<213> ORGANISM: Artificial Sequence
<220> FEATURE:
<223> OTHER INFORMATION: primer

<400> SEQUENCE: 21
gcgtgataca caatgggatg ttggtggtcc cagcagtatt                              40

<210> SEQ ID NO 22
<211> LENGTH: 40
<212> TYPE: DNA
<213> ORGANISM: Artificial Sequence
<220> FEATURE:
<223> OTHER INFORMATION: primer

<400> SEQUENCE: 22
cccattgtgt atcacgccac gctttcatga agcggcagac                              40

<210> SEQ ID NO 23
<211> LENGTH: 40
<212> TYPE: DNA
<213> ORGANISM: Artificial Sequence
<220> FEATURE:
<223> OTHER INFORMATION: primer

<400> SEQUENCE: 23
gcgtgataag caatgggatg ttggtggtcc cagcagtatt                              40

<210> SEQ ID NO 24
<211> LENGTH: 40
<212> TYPE: DNA
<213> ORGANISM: Artificial Sequence
<220> FEATURE:
<223> OTHER INFORMATION: primer

<400> SEQUENCE: 24
cccattgctt atcacgccac gctttcatga agcggcagac                              40

```
<210> SEQ ID NO 25
<211> LENGTH: 40
<212> TYPE: DNA
<213> ORGANISM: Artificial Sequence
<220> FEATURE:
<223> OTHER INFORMATION: primer

<400> SEQUENCE: 25
gcgtgattac caatgggatg ttggtggtcc cagcagtatt                     40

<210> SEQ ID NO 26
<211> LENGTH: 40
<212> TYPE: DNA
<213> ORGANISM: Artificial Sequence
<220> FEATURE:
<223> OTHER INFORMATION: primer

<400> SEQUENCE: 26
cccattggta atcacgccac gctttcatga agcggcagac                     40

<210> SEQ ID NO 27
<211> LENGTH: 40
<212> TYPE: DNA
<213> ORGANISM: Artificial Sequence
<220> FEATURE:
<223> OTHER INFORMATION: primer

<400> SEQUENCE: 27
cgatgaggaa cctttgtttc caccgtcata caaacatggg                     40

<210> SEQ ID NO 28
<211> LENGTH: 40
<212> TYPE: DNA
<213> ORGANISM: Artificial Sequence
<220> FEATURE:
<223> OTHER INFORMATION: primer

<400> SEQUENCE: 28
acaaaggttc ctcatcggtt gagtccggcg actctactcc                     40

<210> SEQ ID NO 29
<211> LENGTH: 40
<212> TYPE: DNA
<213> ORGANISM: Artificial Sequence
<220> FEATURE:
<223> OTHER INFORMATION: primer

<400> SEQUENCE: 29
cgatgaggac cctttgtttc caccgtcata caaacatggg                     40

<210> SEQ ID NO 30
<211> LENGTH: 40
<212> TYPE: DNA
<213> ORGANISM: Artificial Sequence
<220> FEATURE:
<223> OTHER INFORMATION: primer

<400> SEQUENCE: 30
acaaagggtc ctcatcggtt gagtccggcg actctactcc                     40

<210> SEQ ID NO 31
<211> LENGTH: 40
<212> TYPE: DNA
<213> ORGANISM: Artificial Sequence
<220> FEATURE:
```

-continued

<223> OTHER INFORMATION: primer

<400> SEQUENCE: 31
cgatgagatg cctttgtttc caccgtcata caaacatggg                          40

<210> SEQ ID NO 32
<211> LENGTH: 40
<212> TYPE: DNA
<213> ORGANISM: Artificial Sequence
<220> FEATURE:
<223> OTHER INFORMATION: primer

<400> SEQUENCE: 32
acaaaggcat ctcatcggtt gagtccggcg actctactcc                          40

<210> SEQ ID NO 33
<211> LENGTH: 40
<212> TYPE: DNA
<213> ORGANISM: Artificial Sequence
<220> FEATURE:
<223> OTHER INFORMATION: primer

<400> SEQUENCE: 33
gcgcactcac gatgtgtttg aagaagccaa gggcattgcg                          40

<210> SEQ ID NO 34
<211> LENGTH: 40
<212> TYPE: DNA
<213> ORGANISM: Artificial Sequence
<220> FEATURE:
<223> OTHER INFORMATION: primer

<400> SEQUENCE: 34
acacatcgtg agtgcgcaag cgaatgattt tgcgaagtgc                          40

<210> SEQ ID NO 35
<211> LENGTH: 40
<212> TYPE: DNA
<213> ORGANISM: Artificial Sequence
<220> FEATURE:
<223> OTHER INFORMATION: primer

<400> SEQUENCE: 35
agagaatcct ggctggaaat ttgaggccaa gcagacttgt                          40

<210> SEQ ID NO 36
<211> LENGTH: 40
<212> TYPE: DNA
<213> ORGANISM: Artificial Sequence
<220> FEATURE:
<223> OTHER INFORMATION: primer

<400> SEQUENCE: 36
tccagccagg attctctgca accagagatt tcagagaggc                          40

<210> SEQ ID NO 37
<211> LENGTH: 40
<212> TYPE: DNA
<213> ORGANISM: Artificial Sequence
<220> FEATURE:
<223> OTHER INFORMATION: primer

<400> SEQUENCE: 37
gattgccccc gaagcgaacc gtagcttcgt taaaggcgcg                          40

```
<210> SEQ ID NO 38
<211> LENGTH: 40
<212> TYPE: DNA
<213> ORGANISM: Artificial Sequence
<220> FEATURE:
<223> OTHER INFORMATION: primer

<400> SEQUENCE: 38
tcgcttcggg ggcaatctgt ttcttctgaa attcatcttt                          40

<210> SEQ ID NO 39
<211> LENGTH: 40
<212> TYPE: DNA
<213> ORGANISM: Artificial Sequence
<220> FEATURE:
<223> OTHER INFORMATION: primer

<400> SEQUENCE: 39
tggagtaaag tcgccggact caaccgatga gaaacctttg                          40

<210> SEQ ID NO 40
<211> LENGTH: 40
<212> TYPE: DNA
<213> ORGANISM: Artificial Sequence
<220> FEATURE:
<223> OTHER INFORMATION: primer

<400> SEQUENCE: 40
ccggcgactt tactccacgc gcaaattccg acggaagatg                          40

<210> SEQ ID NO 41
<211> LENGTH: 40
<212> TYPE: DNA
<213> ORGANISM: Artificial Sequence
<220> FEATURE:
<223> OTHER INFORMATION: primer

<400> SEQUENCE: 41
gccggaccca accgatgaga aacctttgtt tccaccgtca                          40

<210> SEQ ID NO 42
<211> LENGTH: 40
<212> TYPE: DNA
<213> ORGANISM: Artificial Sequence
<220> FEATURE:
<223> OTHER INFORMATION: primer

<400> SEQUENCE: 42
catcggttgg gtccggcgac tctactccac gcgcaaattc                          40

<210> SEQ ID NO 43
<211> LENGTH: 40
<212> TYPE: DNA
<213> ORGANISM: Artificial Sequence
<220> FEATURE:
<223> OTHER INFORMATION: primer

<400> SEQUENCE: 43
agtctgatcc gaaaattgga catagtctgc tgattctgct                          40

<210> SEQ ID NO 44
<211> LENGTH: 40
<212> TYPE: DNA
<213> ORGANISM: Artificial Sequence
<220> FEATURE:
<223> OTHER INFORMATION: primer
```

-continued

```
<400> SEQUENCE: 44
aattttcgga tcagactcga agatcggcat tggcatgtaa                    40

<210> SEQ ID NO 45
<211> LENGTH: 40
<212> TYPE: DNA
<213> ORGANISM: Artificial Sequence
<220> FEATURE:
<223> OTHER INFORMATION: primer

<400> SEQUENCE: 45
aaagccccgc cggcatttgc ccaagagccg agtagtgctt                    40

<210> SEQ ID NO 46
<211> LENGTH: 40
<212> TYPE: DNA
<213> ORGANISM: Artificial Sequence
<220> FEATURE:
<223> OTHER INFORMATION: primer

<400> SEQUENCE: 46
aatgccggcg gggctttcgc cagcacaatc agttcgctgt                    40
```